(12) United States Patent
Nerín De La Puerta et al.

(10) Patent No.: US 8,741,596 B2
(45) Date of Patent: Jun. 3, 2014

(54) SMART PACKAGING FOR DETECTING MICROORGANISMS

(75) Inventors: M. C. Cristina Nerín De La Puerta, Saragossa (ES); Laura Gutierrez Bartolome, Saragossa (ES); Cristina Sanchez Jarabo, Saragossa (ES)

(73) Assignee: Universidad de Zaragoza, Saragossa (ES)

( * ) Notice: Subject to any disclaimer, the term of this patent is extended or adjusted under 35 U.S.C. 154(b) by 277 days.

(21) Appl. No.: 13/319,048

(22) PCT Filed: Apr. 21, 2010

(86) PCT No.: PCT/ES2010/000176
§ 371 (c)(1),
(2), (4) Date: Dec. 7, 2011

(87) PCT Pub. No.: WO2010/128178
PCT Pub. Date: Nov. 11, 2010

(65) Prior Publication Data
US 2012/0135455 A1 May 31, 2012

(30) Foreign Application Priority Data
May 7, 2009 (ES) .................................. 200930141

(51) Int. Cl.
*C12Q 1/04* (2006.01)
*B65D 79/02* (2006.01)
*A61B 19/00* (2006.01)
*A61B 19/02* (2006.01)
*B65D 71/00* (2006.01)

(52) U.S. Cl.
USPC ............. 435/34; 206/223; 206/439; 206/539; 206/570; 206/572

(58) Field of Classification Search
USPC ............ 435/34; 206/223, 439, 539, 570, 571, 206/572
See application file for complete search history.

(56) References Cited

U.S. PATENT DOCUMENTS

| 2,857,361 | A | * | 10/1958 | Fitz et al. ....................... 523/102 |
| 4,900,681 | A | | 2/1990 | Taffe |
| 2006/0134728 | A1 | | 6/2006 | MacDonald et al. |
| 2007/0264680 | A1 | | 11/2007 | Allef et al. |

FOREIGN PATENT DOCUMENTS

| JP | 7289290 A | 11/1995 |
| WO | WO2006/065350 A2 | 6/2006 |
| WO | WO2008/026119 A2 | 3/2008 |

OTHER PUBLICATIONS

Rakchoy et al. 2009. Antimicrobial effects of vanillin coated solution for coating paperboard intended for packaging bakery products. Asian Journal of Food and Agro-Industry, vol. 2, No. 4, pp. 138-147.*
Written Opinion of International Search Authority of PCT/ES2010/000176, Nov. 29, 2011.

* cited by examiner

*Primary Examiner* — Jon P Weber
*Assistant Examiner* — Kailash C Srivastava
(74) *Attorney, Agent, or Firm* — CUSPA Technology Law Associates; Yi Li (57) ABSTRACT

The present invention relates to novel smart packaging, designed using a novel material comprising a partially polar adsorbent solid base impregnated with a solution of vanillin, which allows the growth of microorganisms in different types of products to be detected visually without having to be in direct contact with the microorganism or with the medium containing same.

19 Claims, 5 Drawing Sheets

SMART PACKAGING FOR DETECTING MICROORGANISMS

FIELD OF THE INVENTION

The present invention is within the food, chemical-pharmaceutical and cosmetic field. Specifically, it refers to a new material consisting of a partially polar adsorbent solid support impregnated with a solution of vanillin and its use as a colorimetric sensor for detecting the presence of microorganisms in food, cosmetics or pharmaceuticals.

BACKGROUND OF THE INVENTION

Every year occur in the world countless cases of hospital admissions due to toxic food infections, resulting from the presence of microorganisms.

For its part, the twenty-first century consumers demand food with high sensory quality and high nutritional value, that is, minimally processed, to the detriment of conventional products. It is obvious that the application of less drastic processing conditions leads to an increase in microbiological risks and therefore, the variability of microbial behavior becomes critical, as the real possibility of survival and development of the residual microbes in any product has to be known, in order to accurately determine their useful life or the microbiological hazards that the producer is willing to assume.

The study of the incidence and prevalence of pathogens in food is in fact one of the priorities of the European Union in terms of food safety. Its purpose is to assess which are the risks actually involved in food, as well as the adoption of microbiological criteria and food security objectives for some types of food.

Currently there is no material marketed with natural compounds that is able to visually detect the presence of a wide range of microorganisms in packaged products. Therefore, neither the consumer nor the retailer or distributor may determine if the packaged products are contaminated or not by microorganisms. In the case of pathogen microorganisms this situation poses a serious health risk. In order to control them it is necessary to resort to microscopic examination and microbiological analysis or planting in selective culture media, thus involving a large consumption of manpower and material. Furthermore, these methods are destructive, thus implying that the analyzed product is no longer available in the commercial chain; they are extremely time-consuming, since from the time the planting is carried out until the microorganisms count is made, there are between 2 and 7 days, regardless of the time needed for pre-enrichment. Such tests also involve significant laboratory cost. In any case, these tests are randomly performed for a representative number of samples, but in no case they can be made for all units of all food items, whereby there is always a potential risk of microbial contamination in a product and not be detected by the producer or final consumer. In pharmaceuticals the risk is much higher, as it is only detected that there has been a problem of this nature when the damage has already been caused, often irreparable.

In recent years, food packaging systems have evolved in response to consumer demands in terms of expiration, preservation of their properties, freshness, appearance, etc. On the one hand, modern marketing methods demand an attractive packaging which communicates something to the consumer in order for him/her to purchase the product. Secondly, the packages have been evolving over the years in response to the profound changes in the lifestyle, and the packaging industry has had to respond to these changes.

The packages have to perform, among others, the following functions:
hold food,
protect food from physical, chemical and microbiological actions
preserve food quality and healthiness,
prevent frauds,
conditioning the product for commercial handling,
display and identify the product,
inform consumers of the characteristics of the food,
extend the useful life, etc.

Lately, due to new requirements in consumer demand, there have been two new packaging concepts, the active packaging and the intelligent packaging. Active and intelligent packages can be seen as the next generation in food packaging.

Active materials and articles in contact with food are defined according to European Directive 1935/2004, as those intended to extend the shelf life or to maintain or improve the condition of packaged food, and which are designed to deliberately incorporate components that transmit substances to the packaged food or their environment or which absorb substances from packaged food or their environment. In recent years there has been an important development in the field of active packaging, with a large number of publications referring to this subject (Rodríguez, A., Battle, R., Nerín, C (2007) *"The use of natural oils as antimicrobial solutions essential in paper packaging. Part II". "Progress in Organic Coatings* 60 (1): 33-38), Rodríguez, A., Nerín, C, and Battle, R (2008). *"New cinnamon-based active paper packaging against Rhizopusstolonifer food spoilage." Journal of Agricultural and Food Chemistry* 56 (15)), López, P., Sánchez C, Battle, R, and Nerín, C. (2007b). *"Development of flexible antimicrobial films using essential oils as active agents." Journal of Agricultural and Food Chemistry* 55 (21): 8814-8824) Gutiérrez, L, Sánchez C, Battle, R.; Nerín, C. (2009). *"New antimicrobial active package for bakery products." Trends in Food Science & Technology* 20 (2): 92-99.

As for intelligent packaging, the aims are different, and this justifies their separation with a special designation. Their action enables a dream in modern world consumer pretensions, with the packaging itself speaking of the quality of the product it contains or events that have marked his processing, acting as an informer of a possible spoilage or degradation as well as of and inadequate maintenance, transportation or distribution. According to the Directive 1935/2004, intelligent packages are defined as those materials that control the condition of packaged food or their surrounding environment.

As "smart packages" will be classified those who use, either the properties or the components of food or of some packaging material as indicators of product quality and history; so far they are essentially time-temperature indicators, microbiological quality indicators, oxygen or carbon dioxide indicators.

The intelligent packaging is therefore defined as one that monitors the condition of packaged food by providing information on the quality of the packaged food during transport and storage, said food condition meaning:
physiological processes (respiration of fruits and fresh vegetables)
chemical processes (lipid oxidation)
physical processes (hardening of bread, dehydration)
microbiological aspects (damaged by microorganisms), and
infection (by insects)

These packages are of great interest in food industry and proof of this is that a great deal of effort is currently being done in the development and research of this type of packaging.

Within this group there are the packages that carry labels, dyes, or enamels, which are used as indicators of the quality, safety or treatment of the packaged product. They are based on physicochemical, enzymatic reactions or others, generally leading to a change of color in the device, thus indicating the harm or change that took place in the food.

Thus, the possibility of using the interaction between food and packaging as something positive can begin to be exploited, i.e., by blocking or inhibiting the causes of food spoilage.

Many of the existing smart indicators are very useful for foodstuff packaging industry, such as time-temperature indicators, package integrity, microbial growth, authenticity of the package, and so on. Several of these are proprietary systems but only a few are commercial, most notably the time-temperature indicators.

There are not so many references relating to the development of smart packages that are able to quickly and efficiently detect the presence of microorganisms in the food at the time of its acquisition or intake. Given that the ingestion of spoiled food from the microbiological point of view is one of the biggest causes of health disease (food poisoning), it is important to detect early, i.e., before intake, packaged products that are infected. Thus, the seller can remove them on time and consumers can avoid their intake without risk to health.

The developments disclosed in relation to this type of smart packages, require direct contact between the microorganism and the sensor, which acts as a smart package, such as in patents EP1326653, WO03093784, WO2008026119, (Kimberly-Clark Worldwide, INC), wherein a chromogenic detector is used, or WO0013009, (Johnson Matthey Public Limited Company), wherein metal complexes are used as reaction supports. In document Desbordes, J: CONIVE, L Prevot. A. *Annales Francaises Pharmaceutiques* 1972, 30 (7-8), 507-518 vanillin colored reaction in sulfuric and phosphoric acid is used to identify the presence of lipids in bacterial studies, and finally identifying the fatty acids by thin layer chromatography and gas chromatography. Again, in this development, the direct contact between the bacterium and the reagent is necessary to produce the reaction. Further, the manufacturing system of this type of sensors is of great complexity, which makes difficult its manufacture on an industrial scale. Moreover, the actuating mechanism is complex and requires first the generation of a colored compound, which will disappear when contacting microorganisms. In addition, the compounds used as chromogens, are chemical compounds that in some cases require special conditions such as acidification, or complex chemical compounds in order for the reaction to take place, several of which cannot be used today in contact with food or have a major limitation in their concentration. In any case, natural compounds are used as main chromogenic compounds, much less compounds accepted as a food additives, with the technological and health benefits this entails.

In view of the deficiencies of the packages so far described, the authors of the present invention, after considerable research, have developed a new material which comprises a partially polar adsorbent solid support impregnated in a solution of vanillin that can be used as colorimetric sensor for the detection of microorganisms in packaged products of different nature.

Advantageously, vanillin (3-methoxy-4-hydroxybenzaldehyde), authorized as a food additive, can detect the growth of microorganisms through a simple and easily identifiable chromogenic reaction. It also acts on the sensor without having to be in direct contact with the food or packaged product, however to take place it needs the presence of a small concentration of moisture in vapor phase.

Vanillin is a natural compound found in many vegetables, especially in vanilla pod. It is industrially obtained from eugenol, the main constituent of clove oil. It is also obtained by oxidation of lignin, a complex polymer found in woody tissue of plants.

Vanillin is widely used as a flavoring agent in foods, especially in pastry. It is also used in the pharmaceutical industry as a gastric stimulant and in perfumery.

There are some references in the state of the art which also cite the use of vanillin as a precursor of other reagents, but it needs a long synthesis process and mixing with solvents such as ethanol and reagents such as concentrated hydrochloric acid, piperidine, methyl iodide or others. For example, in document WO2008026119, vanillin is not the major component of the invention, but it requires the presence of another compound in the reaction for the color change to take place.

Other methods, using vanillin as a detector of the presence of microorganisms need to strongly acidify the medium with HCl, with the drawbacks that this entails, and also they are only able to detect the presence of those microorganisms that are capable of producing indole. Thus, document Ferlin, H. J. and Karabiner (*J.V. Euclides* 1954, 14, 345-353) discloses a medium containing tryptophan as a source to isolate *E. coli* and *P. vulgaris* from mixtures based on differences in the production of indole from tryptophan. With that, they also developed a reagent for performing the indole test. Under these conditions, they used the addition of a 0.25% vanillin solution in concentrated hydrochloric acid to produce a violet color with indole, by direct contact and in liquid phase. That is, indole producing microorganisms were to be found in said solution, producing the indole that gives rise to the chromogenic reaction.

In the light of these drawbacks, one of the main advantages of the present invention is precisely the use of a not harmful natural compound, food additive, such as vanillin, and the capacity to detect the presence of microorganisms without the need for a direct contact between the microorganism and the packaging material.

Its application is aimed at solving a problem that poses a great risk to society, as is the presence of pathogenic microorganisms in food, cosmetics and pharmacy products, or other packaged products.

The material of the invention is incorporated into the packaging material of food, or any other products susceptible to contamination by microorganisms, so that by an easily recognizable color change (from colorless to purple), the consumer is able to reject the product and avoid the food intake or the use of products infected and contaminated with microorganisms harmful for health.

On the other hand, it is a system that greatly contributes to the quality control of packaged goods by timely removing contaminated batches, thereby preventing them from reaching the final consumer as well as all the problems and costs incurred by potential returns. The sectors involved in the development and implementation of this new device would be on one hand the packaging industry, which would be responsible for manufacturing and placing on the market the material incorporated in the package, and on the other hand, the food, cosmetic or pharmaceutical industries. This sector has to deal with the optimization of location of the material inside the package, taking into account the industrial packaging process, in order to achieve a location easily visible to the end user and which does not interfere with the packaged product or impedes the industrial packaging process.

The main advantage of using a sensor such as the one presented as invention is the possibility that it offers the consumer to know that the food he or she is about to eat or the product he or she is about to use is free of microorganisms, at the time of the acquisition and ingestion thereof and thus he or she can refrain from consuming it and reject the product.

OBJECT OF THE INVENTION

Firstly, an object of the invention is a material comprising a partially polar adsorbent solid support impregnated in a solution comprising vanillin.

Another object of the invention is the use of said material as a colorimetric sensor for visually detecting the growth of microorganisms, wherein said sensor does not require direct contact with microorganisms or with the medium containing them to produce the color change.

Finally, it is also an object of the invention the use of vanillin as a colorimetric reagent for visually detecting the growth of microorganisms.

DESCRIPTION OF THE INVENTION

The present invention contemplates a new intelligent packaging, designed from a new material that allows visual detection of the growth of microorganisms in products of different nature without being in direct contact with the organism or the medium containing it.

Thus, in a major aspect of the invention, it is contemplated said material, which comprises a partially polar adsorbent solid support impregnated in a solution comprising vanillin.

The presence of vanillin in the composition of the material allows the growth of microorganisms to be detected by a simple and easily identifiable chromogenic reaction. The color change (from colorless to purple) under the test conditions clearly relates to the presence of microorganisms, both in pure cultures, performed in Petri dishes, and in food, such as for example homemade, preservative-free mayonnaise, in drugs or cosmetics.

Vanillin is a natural compound that reacts in the presence of microorganisms. In the absence of vanillin the reaction colored does not occur. The reaction is irreversible and the color produced increases in intensity while the microbial growth continues to be produced.

In a particular embodiment, the vanillin solution comprises ethanol. The minimum concentration of vanillin needed to make visible the colored reaction is 10%, preferably from about 10 to about 50% in ethanol.

The reaction requires an aqueous medium or at least moisture to be visible, lasting and irreversible and therefore serve as a colorimetric detector. Hence, the solid support must be from a partially polar adsorbent material capable of retaining the moisture released by the food itself in the vapor phase, preferably using paper or cardboard.

In the event that the vanillin was incorporated into a hydrophobic medium, the reaction would not be permanent, because the moisture would condense on the hydrophobic support and, although it would likewise be colored, would not remain in that the drop of dew would fall by gravity. Therefore, it would not be an irreversible and stable support.

As mentioned above, the disclosed features of the invention material render it suitable for the visual detection of microbial growth, therefore in another key aspect of the invention the use of this new material is contemplates as colorimetric sensor for the visual detection of microorganism presence.

The sensor reaction takes place in the vapor phase, therefore the vanillin needs not to be in direct contact with the microorganism or the medium containing it. Thus, the sensor and the microorganisms may be away from each other, with the only contact between them being through a vapor phase.

The fact that the sensor does not require direct contact with the organism is very advantageous, and an important difference from the sensors disclosed in the state of the art, as in this way the compounds exhaled by microorganisms in their metabolism reach the vapor phase and through it they reach the sensor where the chromogenic reaction takes place. This enables the sensor to be placed on the lid or adhered to the package or being part of it, but at a distance. It also has the advantage that under these conditions, i.e., acting in the vapor phase, is able to respond to the presence of microorganisms in any part of the product where they be present, not being limited to a fraction or portion thereof, as when direct contact is required.

Furthermore, the fact that the color change occurs due to the transfer or diffusion of compounds from microorganisms in the vapor phase can achieve high sensitivity, which means that the sensor responds to the appearance of the first colonies of microorganisms in the medium.

In the presence of a microbial concentration equal to or greater than 10 colony forming units per ml or per mg (CFU/ml, CFU/mg) of microorganism-containing food, the sensor changes color irreversibly, from colorless (or white, due to the paper or solid support) to pink-violet. The intensity of color depends on the concentration of microorganisms.

The sensor allows visually detecting the growth of a broad spectrum of microorganisms such as molds, yeasts and/or bacteria.

All microorganisms generating indole in their metabolism react with vanillin. In addition, other organisms that do not produce indole in their metabolism, such as *Salmonella* and *Pseudomonas* spp., are also positive to the identification reaction with vanillin, whereby the reaction would not be specific "indole-vanillin," but it would be defined as a more generic "nitrogen compounds-vanillin" reaction.

The detection of microorganisms by the smart sensor or system of the invention can be carried out in a packaged product. The packaged product may be different in nature, preferably is a food, pharmaceutical or cosmetic product.

Thus, in particular embodiments, the intelligent system formed by the material as a sensor can be used as a packaging material itself or applied in the form of paper-based label, preferably in a self-adhesive format, placed on the inner face of the package, which can be plastic or other material, so that it is exposed to the atmosphere generated inside the package. The package should be from transparent and colorless material in that area, in order to allow the viewing of the color change that will occur in the presence of microorganisms.

Finally, another major aspect of the invention contemplates the use of vanillin as a colorimetric reagent for visually detecting the growth of microorganisms in the vapor phase, i.e., without direct contact between the vanillin and the microorganism.

EXAMPLES

The activity of the sensor based on different support materials and experimental conditions was studied. This allowed clear visualization of sensor operation at the macroscopic level.

Figure 1:
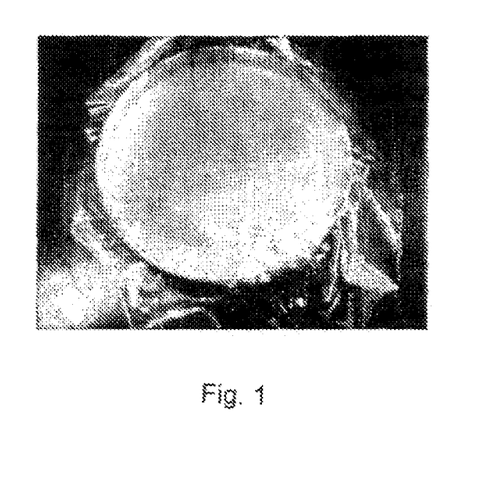
FIG. 1. Application of sensor material in a polypropylene film. *E. coli* culture.

FIG. 1 shows the application of a polypropylene (PP) film impregnated in a vanillin solution in a culture of *E. coli*. Although the formulation used was the appropriate one designed for this sensor, no color change was observed. The reason for the absence of response (color change) is that the material did not absorb the moisture or the compounds, or what is the same thing, the reaction with the formulation containing vanillin was not retained on the support, as it was in a non-polar medium, imbibed in the polypropylene (PP). In fact, there was a colored halo covering the PP film but eventually condensed and fell off the PP film, considering this non-polar or non-adsorbent support as invalid to be used as support for the sensor.

Figure 2:
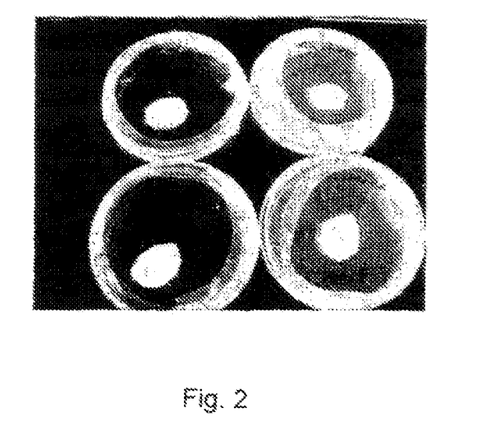
FIG. 2. Application of sensor material in paper filters in the absence of microorganisms (blank), with culture medium (left column) and without culture medium (right column).

FIG. 2 shows that blank tests (no microorganisms) were carried out, using several paper support filters soaked in the vanillin solution in the presence of culture media (left column) and in the absence of culture media (right column). It was shown that in the absence of microorganisms, the presence of culture medium is not sufficient for the reaction to take place.

Figure 3:
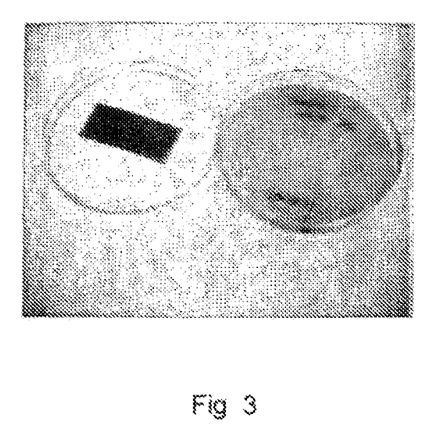
FIG. 3. Application of sensor material in an adhesive paper label. *E. coli* culture.

FIG. 3 shows the application of the sensor material of the invention to an auto-adhesive label for detecting the presence of microorganisms in a culture of *E. coli*, whereby the color change of the sensor was observed.

Figure 4:
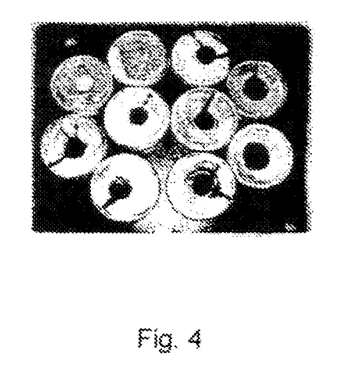
FIG. 4. Application of sensor material in paper filters in the presence of microorganisms (*E. coli*) or absence of microorganisms (blank). The culture medium is Müller-Hinton.

FIG. 4 shows the application of the sensor material to several paper filters in different cultures of *E. coli* and in a blank culture, i.e., without microorganism. The culture medium was Müller-Hinton. It was observed that the coloring occurred in all cultures of *E. coli*, while in the only blank culture no color appeared.

To extend the study, the behavior of the invention material against a wide range of microorganisms was assessed, in order to determine the minimum concentration required for the sensor to work properly.

Tests were conducted to study the efficacy of the sensor in the following microorganisms:

Molds
*Aspergillus flavus* (Spanish Type Culture Collection, CECT, 2687)
*Penicillium roqueforti* (Culture Collection of Fungi, IBT, 21319)
*Eurotium repens* (IBT 1800)
*Penicillium islandicum* (CECT 2762)
*Penicillium ammune* (IBT 21314)
*Penicillium expansum*
*Penicillium nalgiovensis*

Yeasts
*Candida albicans* (American Type Culture Collection, ATCC, 64550)
*Debaryomyces hansenii* (CECT 10353)
*Zygosaccharomyces rouxii* (CECT 11928)
*Botrytis cinerea*

Bacteria
*Enterococcus faecalis* (ATCC 29212)
*Listeria monocytogenes* (ATCC 7644)
*Bacillus cereus* (CECT 495)
*Staphylococcus aureus* (ATCC 29213)
*Salmonella choleraesuis* (CECT 4000)
*Yersinia enterocolitica* (CECT 4315)
*Escherichia coli* (ATCC 29252)
*Pseudomonas aeruginosa* (ATCC 27853)

Positive reactions were observed both among bacteria, as in molds and yeasts. Of the microorganisms tested that gave positive reaction in the following table (Table 1) there are shown those in which the microorganism concentration value can be clearly expressed, depending on the concentration of inoculated microorganisms and the time needed for the color change in the sensor.

TABLE 1

Color change in terms of concentration

| Bacterium | Incubation days | MCC (cfu per mg/ml) | MCD (cfu per mg/ml) |
| --- | --- | --- | --- |
| P. aeruginosa | 1 | 10 | $10^7$ |
|  | 2 | 10 | $10^2$ |
|  | 3 | 10 | 10 |
| E. coil | 1 | 10 | $10^7$ |
|  | 2 | 10 | $10^2$ |
|  | 3 | 10 | 10 |
| E. faecalis | 1 | 10 | $10^6$ |
|  | 2 | 10 | $10^2$ |
|  | 3 | 10 | $10^2$ |
|  | 4 | 10 | 10 |
| B. cereus | 1 | 10 | $10^6$ |
|  | 2 | 10 | $10^4$ |
|  | 3 | 10 | $10^2$ |
|  | 4 | 10 | $10^2$ |
| S. aureus | 1 | 10 | $>10^7$ |
|  | 2 | 10 | $10^5$ |
|  | 3 | 10 | $10^4$ |
|  | 4 | 10 | $10^4$ |
| Y. enterocolitica | 1 | 10 | $>10^7$ |
|  | 2 | 10 | $>10^7$ |
|  | 3 | 10 | $10^7$ |
|  | 4 | 10 | $10^6$ |

MCC: Minimum inoculated concentration:
MCD: Minimum detectable concentration

The studies were completed by studying the effect of different culture media in changing the color of the adsorbent support containing the sensor. Due to the high consumption of resources, we chose two microorganisms as representatives of each group and three generic culture media that allow the growth of all microorganisms, but with a different content of protein source, as differentiating characteristic. The selected media were Müller-Hinton (M.H), Malt Extract Agar (M.E.A.) and T.S.A. (Tryptone Soya Agar). The time of the study was prolonged to one year. The following tables (2 and 3) summarize the selected microorganisms and culture media. The differences in the composition of culture media represent different concentrations of nutrients and thus simulates food situation in which the nutrients for the microorganisms will be different from each other.

TABLE 2

Microorganisms

| GROUP | MICROORGANISMS | CULTURE MEDIUM |
|---|---|---|
| GRAM POSITIVE | B. cereus and E. faecalis | M. H, M.E.A. and T.S.A. |
| GRAM NEGATIVE | P. aeruginosa and S. cholerasuis | M. H, M.E.A. and T.S.A. |
| YEASTS | C. albicans | M. H, M.E.A. and T.S.A. |
| MOLDS | A. flavus and P. roqueforti | M. H, M.E.A. and T.S.A. |

TABLE 3

Composition of the different culture media that were used

| | MULLER-HINTON | T.S.A. | SABOURAUD DEXTROSE AGAR | M.E.A |
|---|---|---|---|---|
| | Starch 1.5 g | Sodium chloride 5 g | D(+) Glucose 40 g | Malt Extract 13 g |
| | Beef infusion 2 g | Casein peptone 15 g | Chloramphenicol 50 mg | Dextrin 2.5 g |
| | Hydrolyzed casein peptone | Soy peptone 5 g | Peptone mixture 10 g | Gelatin peptone 5 g |
| | | Agar 15 g | Agar 1 g | Agar 15 g |
| Final pH | 7.2 | 7.3 +/− 0.2 | | 5.5 +/− 0.2 |

Figure 5:
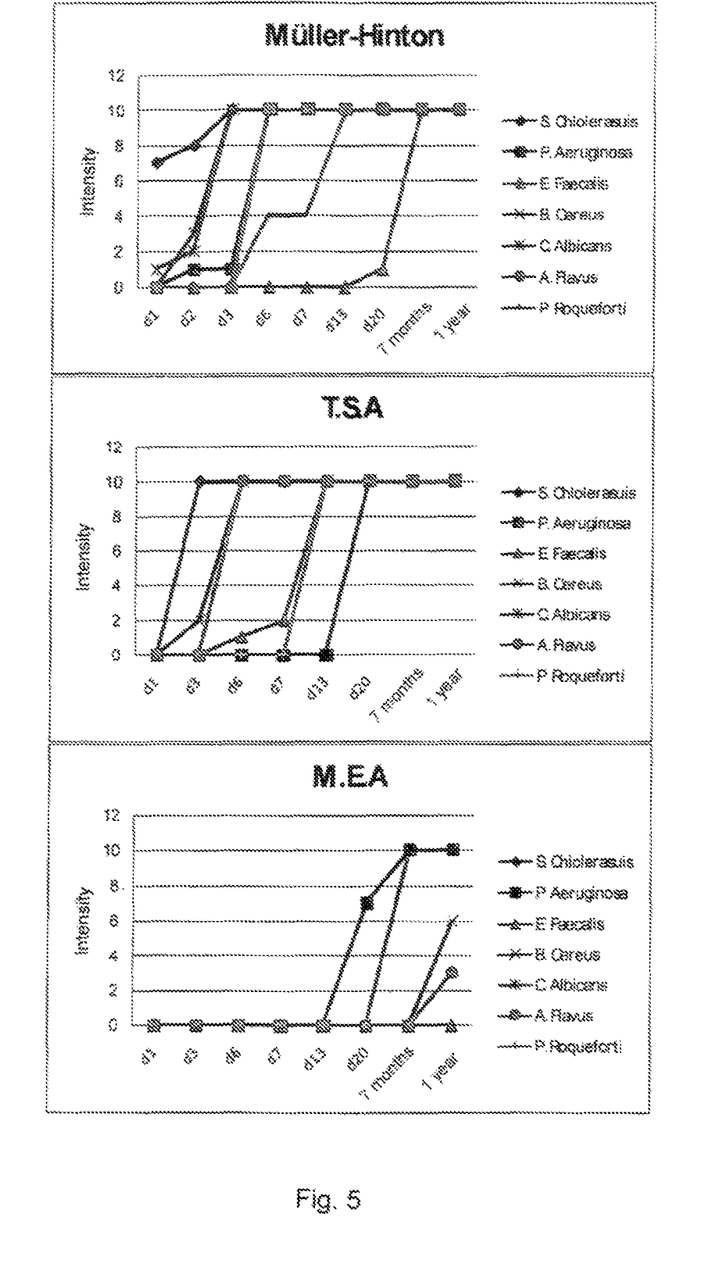
FIG. 5. Graph of days required to achieve coloring in different media (Müller-Hinton, TSA, M.E.A.) for different microorganisms.

The graphs of FIG. 5 show the days that were required for the filter to achieve a final, substantially black color (purple or very intense violet) for the different organisms in different media studied. Intensification of the color is observed depending on the concentration of microorganisms.

Following this study it was concluded that the culture medium in which microorganism growth occurs significantly affects the color change. This change was faster in Müller-Hinton medium with a higher content of nitrogen compounds, followed by T.S.A. and M.E.A., the change was much slower.

The main difference between these media is the content of nitrogen compounds. In the case of Müller-Hinton, beef and casein supply nitrogen compounds, vitamins, carbon, sulfur and amino acids. For T.S.A., soybean enzymatic digestion provides nitrogen, vitamins and minerals, while M.E.A. is high in polysaccharides and as the sole nitrogen source it has peptone and in lesser amounts than those present in the other two media. This affects the intensity of the reaction that takes place with vanillin and thus the color change, since in those cases in which microorganisms grow quickly because they find a great amount of nutrients, the reaction occurs earlier, leading to a color change in the sensor earlier in time and more intense for the same time as in other cases.

We investigated the reaction mechanism that took place, proving that microorganisms generating indole in their metabolism gave a positive reaction, suggesting that it was a colored compound due to chemical reaction between indole and vanillin. However, microorganisms that do not produce indole, such as Salmonella and Pseudomonas spp, also gave a positive reaction with vanillin.

Additional assays were conducted to demonstrate the effectiveness of vanillin in the detection of microorganisms and to rule out that the coloration change was due to a change in pH or due to the presence of $CO_2$ from the metabolism of microorganisms. In these tests we selected Müller-Hinton as a culture medium, since it was the one that generated a quicker color change reaction for all cases.

Effect of $CO_2$:

The microorganisms in growth and respiration release $CO_2$. Because of the abundance and volatility of this compound we studied the effect it had on the color developed by labels impregnated with vanillin.

This was achieved with the preparation of culture media plates and labels impregnated with the vanillin solution to study, but without the presence of microorganisms. The incubation was performed in anaerobic jars and under anaerobic and microaerophilic conditions, by using sachets generating these atmospheres. The plates were not sealed in the inside of the jar, so that the $CO_2$ could penetrate.

The test was repeated in triplicate and showed that after 50 days at 37° C., in the Müller-Hinton plates and the filter containing vanillin there was no color change on the disc.

Therefore, it was concluded that the color change is not caused by the presence of $CO_2$.

Effect of pH:

The pH of the medium was superficially modified. Acetic acid was added to three plates and NaOH to other three, and the effect that these acid compounds or bases could have on the sensor, in the absence of microorganisms, was observed. It was observed that after three months, there was no color change. There was no direct contact between the filters and the acidifying or basifying agents.

In the following assay, the acid and the base were directly added to the filter, to which vanillin had been previously added. The rest of the plate preparation was identical for all cases, without seeding of the microorganism. There was also no color change.

Complementary to these assays the acid and the base were directly added to the ethanol-vanillin mixture, and the filter was impregnated with this mixture that was placed on the plates as in all previous tests.

It was observed that there was no color change in any of the filters after a month. We therefore concluded that the color change of the sensor is not produced by a pH change. Three months later there is still no color change.

Figure 6:
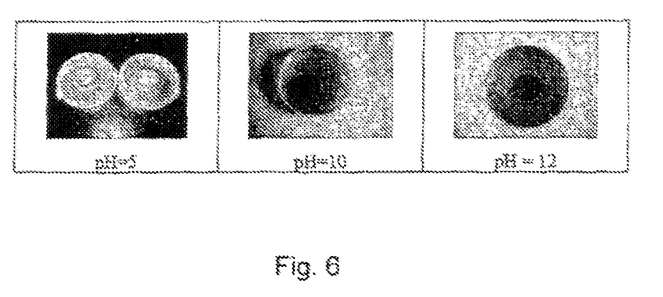
FIG. 6. Application of the sensor material to a paper filter at different pHs in a culture without microorganisms, Müller-Hinton medium.

However, when the culture medium pH was changed intrinsically after 5 days, it was observed that there was a change of color in the samples that were in the vapor phase with the medium at pH 12 and pH 10 (FIG. 6).

The growth of microorganisms also generated a change in the final pH of the medium, being a basic pH value around 10.

Analysis of the Compounds Responsible for Color Change

The evolution of vanillin and the new compounds that appeared after the reaction was analyzed by chromatographic techniques.

To see the evolution of vanillin, SPME (solid phase microextraction) and GC-MS (gas chromatography-mass spectrometry) analyses were performed.

Figure 7:
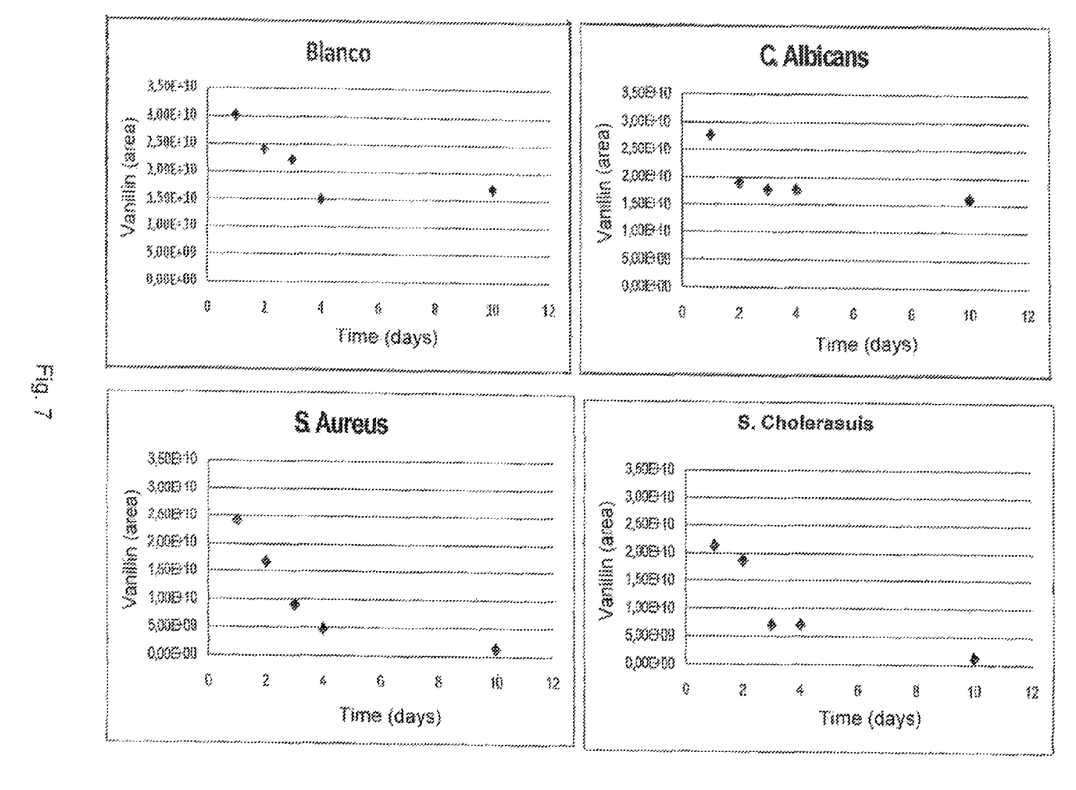
FIG. 7. Graph of the evolution of vanillin concentration in time with a) absence of microorganisms (blank); b) *Candida albicans*; c) *Staphylococcus aureus* and d) *Salmonella cholerasuis*.

As can be seen (FIG. 7) there was a decrease in the concentration of vanillin in all cases. This decrease was greater for the case of S. aureus and S. cholerasuis, which are also the microorganisms that cause a more rapid and intense color change. With this technique we could not detect the presence of new compounds responsible for color change, in that probably the colored compound generated is not volatile. However the concentration of vanillin decreased, indicating that a reaction thereof with a compound generated by the growth of microorganisms took place, causing the appearance of the new colored compound.

The invention claimed is:

1. A smart package for detection of growth of microorganisms in a packaged product comprising a colorimetric sensor material positioned at an inner face of the package at an area not in contact with a product to be held in the package and exposed to atmosphere inside the package, said sensor material comprising a partially polar adsorbent solid support and vanillin impregnated in the solid support, wherein the sensor material exhibits a detectable color change when microorganisms are present in the package, caused by reaction of vanillin with compounds in vapor generated by metabolism of the microorganisms in the package, thereby indicating the presence of the microorganisms in a packaged product.

2. The smart package according to claim 1, wherein the solid support is paper.

3. The smart package according to claim 1, wherein the area of the package where the sensor material is positioned is transparent, permitting visually viewing the color change.

4. The smart package according to claim 1, wherein the sensor material is placed on a lid of the package, or adhered to the inner face of the package.

5. The smart package according to claim 1, wherein the sensor material forms a part of the package.

6. The smart package according to claim 1, wherein the sensor material is formed by impregnating the solid support in a solution having a concentration of vanillin of at least 10%.

7. The smart package according to claim 1, wherein the sensor material is formed by impregnating the solid support in an ethanol solution having a concentration of vanillin from about 10 to about 50%.

8. A method of detection of growth of microorganisms in a packaged product comprising:
   holding a product in a smart package, said smart package having a colorimetric sensor material positioned at an inner face of a package at an area not in contact with the product and exposed to atmosphere inside the package, said sensor material comprising a partially polar adsorbent solid support and vanillin impregnated in the solid support; and
   visually detecting a color change of the sensor material caused by reaction of vanillin with compounds in vapor generated by metabolism of microorganisms in the package, thereby identifying the presence of the microorganisms in the packaged product.

9. The method according to claim 8, wherein the microorganisms include molds, yeasts and/or bacteria.

10. The method according to claim 8, wherein the color change is visually detectable at a concentration of microorganisms equal or higher than 10 CFU per ml or mg of the product contained in the package.

11. The method according to claim 8, wherein an intensity of changed color on the sensor material correlates with a concentration of microorganisms in the package.

12. The method according to claim 8, wherein the color change on the sensor material is irreversible.

13. The method according to claim 8, wherein the product contained in the package includes a food, pharmaceutical, or cosmetic product.

14. The method according to claim 8, wherein the sensor material is formed by impregnating the solid support in a solution having a concentration of vanillin of at least 10%.

15. The method according to claim 8, wherein the sensor material is formed by impregnating the solid support in an ethanol solution having a concentration of vanillin from about 10 to about 50%.

16. The method according to claim 8, wherein the solid support is paper.

17. The method according to claim 8, wherein the area of the package where the sensor material is positioned is transparent, permitting visually viewing the color change.

18. The method according to claim 8, wherein the sensor material is placed on a lid of the package, or adhered to the inner face of the package.

19. The method according to claim 8, wherein the sensor material forms a part of the package.

\* \* \* \* \*